United States Patent [19]

Nakayama et al.

[11] Patent Number: 4,562,738

[45] Date of Patent: Jan. 7, 1986

[54] AUTOMATIC FLAW DETECTION DEVICE

[75] Inventors: Kazuo Nakayama; Yukio Naito; Eiji Munesue, all of Hyogo, Japan

[73] Assignee: Mitsubishi Denki Kabushiki Kaisha, Tokyo, Japan

[21] Appl. No.: 596,700

[22] Filed: Apr. 4, 1984

[51] Int. Cl.⁴ ............................................. G01N 29/04
[52] U.S. Cl. ...................................... 73/622; 73/633;
73/637; 73/640; 324/228
[58] Field of Search ................. 73/618, 622, 633, 634,
73/637–640; 324/228

[56] References Cited

U.S. PATENT DOCUMENTS

| | | | |
|---|---|---|---|
| 3,415,111 | 12/1968 | Chattaway et al. | 73/622 |
| 3,533,281 | 10/1970 | Hetherington | 73/640 |
| 3,561,258 | 2/1971 | Ashford | 73/622 |
| 3,854,326 | 12/1974 | Hetherington et al. | 73/640 |

*Primary Examiner*—Howard A. Birmiel

*Attorney, Agent, or Firm*—Oblon, Fisher, Spivak, McClelland & Maier

[57] ABSTRACT

An automatic flaw detection apparatus comprises a supporting frame; a rotational frame supported inside the supporting frame in a freely rotatable manner by means of bearings; a hollow shaft which is supported by and inside the rotational frame, through the interior of which passes a material to be inspected; a holder which is disposed within the hollow shaft extending in the longitudinal direction of the axis of the hollow shaft and rotates in association with the hollow shaft, the a sensor incorporated in the holder to detect any defect in the material to be probed; and a signal transmission device which is placed between the hollow shaft and the rotational frame and comprises a stator section supported by the supporting frame and a rotor section supported by the hollow shaft or the rotational frame to be electrically in association with the stator section, and which transmits flaw detection signal from the sensor to the outside.

4 Claims, 3 Drawing Figures

AUTOMATIC FLAW DETECTION DEVICE

BACKGROUND OF THE INVENTION

1. Field of the Invention

This invention relates to an ultra-sonic automatic flaw detection device which detects automatically any defects in a material to be probed such as steel material, etc. by use of, for example, an ultra-sonic searching unit as a sensor.

2. Description of Prior Art

As a device of this kind, there has so far been known such one as shown in FIG. 1 of the accompanying drawing.

In the drawing, a reference numeral 1 designates a supporting frame which supports the entire device; a numeral 2 refers to a bearing supporter mounted on the supporting frame 1; a numeral 3 refers to a hollow shaft which is fitted and supported in a freely rotatable manner on this bearing supporter 2 through bearings 4, 4 such as, for example, ball bearings, etc., and through the interior of which passes a material 5 to be probed. The bearings 4, 4 are disposed in the neighborhood of both end parts of the hollow shaft 3. A numeral 6 refers to a signal transmission device which is interposed between the bearing supporters 2, 2, confronts to the hollow shaft 3, and transmits flaw detection signals from ultra-sonic searching units 9 to be mentioned later to the outside. The signal transmission device 9 is constructed with a rotor section 6a mounted on and around the outer periphery of the hollow shaft 3 between the bearings 4, 4 and a stator section 6b fixed on the supporting frame 1 in a manner to be opposite to the rotor section 6a, both these sections being made electrically cooperative. A reference numeral 7 designates a flaw detection signal repeater mounted on one end part of the hollow shaft 3. A reference numeral 8 designates a holder for searching units, which extends in the axial direction and opposite to the hollow shaft 3 through the flaw detection signal repeater 7, and rotates in association with rotation of the hollow shaft 3. A numeral 9 refers to a sensor comprising ultra-sonic searching units incorporated in the searching unit holder 8 (the sensor will hereinafter be called "ultra-sonic searching unit"). A reference numeral 10 denotes a water supply device which is mounted on the bearing supporter 2 at the other end part of the hollow shaft 3, and is to supply water for the flaw detection into a space gap between the ultra-sonic searching units 9 and the material 5 to be probed through a water supply passage formed consecutively in the hollow shaft 3, the flaw detection signal repeater 7, and the searching unit holder 8. A reference numeral 11 represents a belt pulley which is fitted on and around the outer periphery of the hollow shaft 3 at the other end part thereof; a numeral 12 refers to a drive motor mounted on one part of the supporting frame 1; a reference numeral 13 designates a belt extended between the rotational shaft of the drive motor 12 and the belt pulley 11; and a numeral 14 refers to pinch rollers to perform alignment of the material 5 to be probed.

In the following, the operations of the conventional automatic flaw detection device of the above-described construction will be explained. The ultra-sonic automatic flaw detection device is installed in a inspection line for the material 5 to be probed, such as steel material, so that the materials 5 may pass sequentially through it. First of all, the drive motor 12 is actuated to rotate the hollow shaft 3 through the belt 13 and the belt pulley 11. In association with rotation of this hollow shaft 3, there rotate both searching unit holder 8 mounted on the hollow shaft 3 through the flaw detection signal repeater 7 and the ultra-sonic searching units 9 embedded in the searching unit holder 8. In the next place, a material 5 to be probed is conveyed from the inspection line and passes through the center of the searching unit holder 8 after alignment of the material 5 to be probed by way of the pinch rollers 14, 14. During passage of the material 5 to be probed through the center of the searching unit holder 8, water for the flaw detection is supplied from the water supply device 10 so as to fill the space gap between the ultra-sonic searching units 9 and the material 5 to be probed. By thus causing the material 5 to be probed to pass through the center of the searching unit holder 8 in rotation, the material 5 to be probed is sensed in a spiral form by means of the ultra-sonic searching units 9 embedded in the searching unit holder 8. The flaw detection signals from the ultra-sonic searching units 9 are transmitted from the rotor section 6a of the signal transmission device 6 to the stator section 6b through the flaw detection signal repeater 7, and then led outside.

With the above-described conventional device, however, the searching unit holder 8 extends in the longitudinal direction of and opposite to the hollow shaft 3, that is, it is mounted outwardly of the device in a jut-out condition, with the consequent elongation of the total length of the device. Accordingly, the spacing for arranging the pinch rollers 14, 14 becomes wide, and, when the distal end of the material 5 to be probed is about to pass through the searching unit holder 8 as shown in FIG. 3, if flexure or curving of the material 5 to be probed is large, it gets in contact with the searching unit holder 8 to make it impossible to carry out the flaw detection, and various other disadvantages.

SUMMARY OF THE INVENTION

The present invention has been made in view of the disadvantages inherent in the conventional device as mentioned in the foregoing, and aims at providing an automatic flaw detection device capable of shortening the total length of the device by disposing a rotational frame inside a supporting frame and by disposing inside the rotational frame a hollow shaft which supports a searching unit holder having the sensors embedded therein, the researching unit holder rotating in association with the hollow shaft and extending the same in and along the axial direction thereof.

According to the present invention in general aspect of it, there is provided an automatic flaw detection apparatus comprising a supporting frame; a rotational frame supported inside the supporting frame in a freely rotatable manner by means of bearings; a hollow shaft which is supported by and inside the rotational frame, through the interior of which passes a material to be inspected; a holder which is disposed within the hollow shaft extending in the longitudinal direction of the axis of the hollow shaft and rotates in association with the hollow shaft, a sensor incorporated in the holder to detect any defect in the material to be probed; and a signal transmission device which is placed between the hollow shaft and the rotational frame and comprises a stator section supported by the supporting frame and a rotor section supported by the hollow shaft or the rotational frame to be electrically in association with the stator section, and which transmits flaw detection signal from the sensor to the outside.

The foregoing object, other objects as well as the specific construction and founction of the automatic flaw detection device according to the present invention will become more apparent and understandable from the following detailed description of a preferred embodiment thereof, when read in conjunction with the accompanying drawing.

BRIEF DESCRIPTION OF THE ACCOMPANYING DRAWING

DETAILED DESCRIPTION OF A PREFERRED EMBODIMENT

An embodiment of the present invention will be described with reference to FIG. 2.

Figure 1:
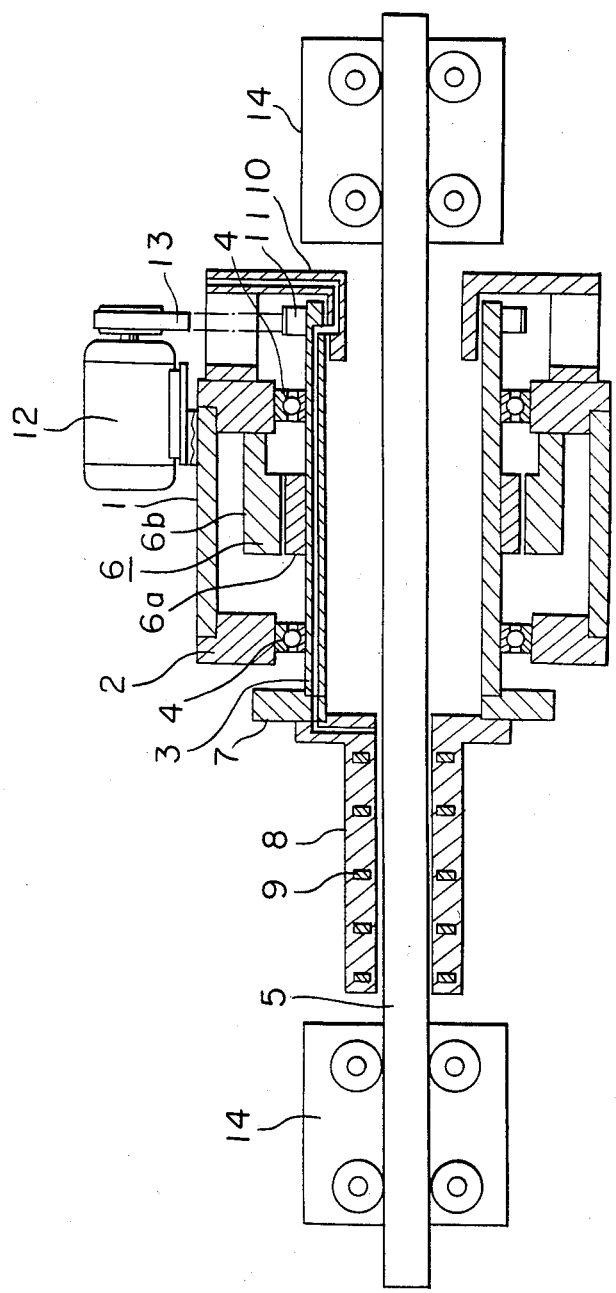
FIG. 1 is a longitudinal cross-sectional view showing a conventional automatic flaw detection device.
Figure 2:
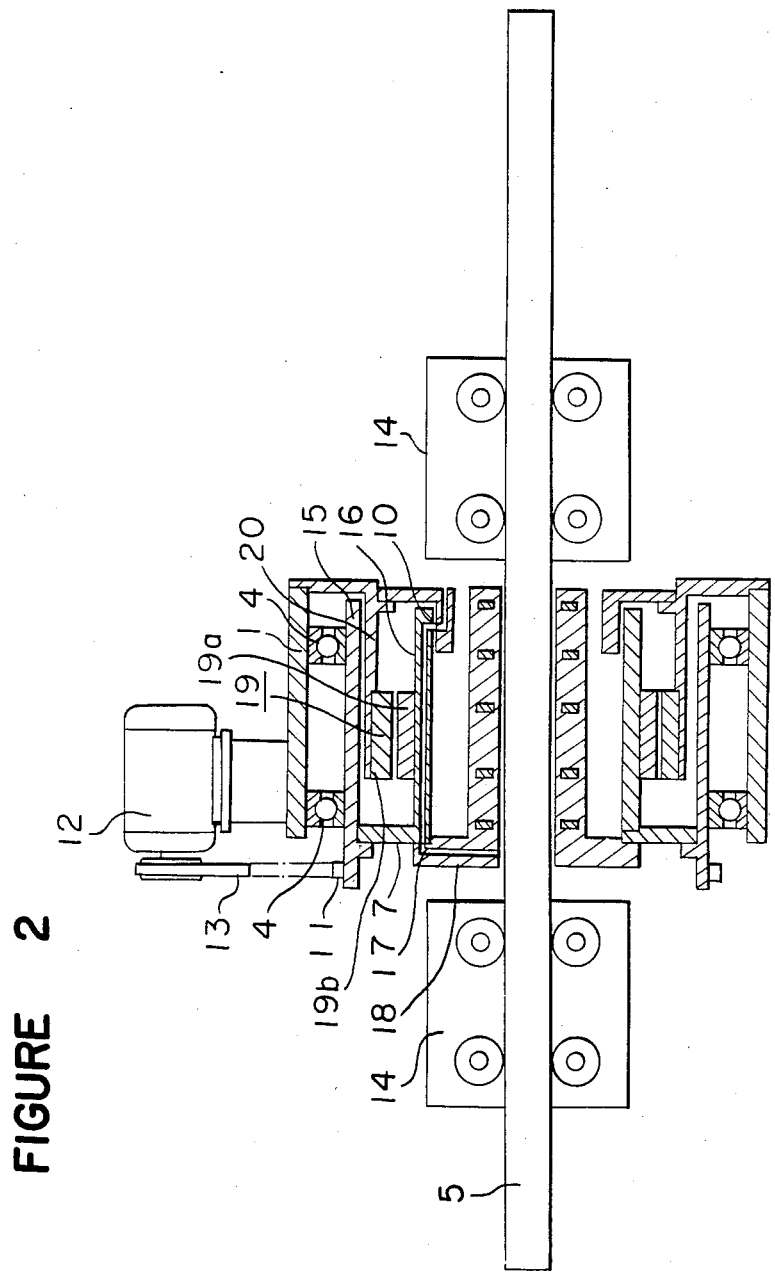
FIG. 2 is also a longitudinal cross-sectional view showing one embodiment of the automatic flaw detection device according to the present invention.

In FIG. 2, a reference numeral 1 designates a supporting frame; a numeral 4 refers to bearings; a numeral 5 denotes a material to be probed; a numeral 7 indicates a flaw detection signal repeater; a numeral 10 designates a water supply device; a numeral 11 represents a belt pulley; a numeral 12 refers to a drive motor; a numeral 13 denotes a belt, and a numeral 14 indicates pinch rollers, all of which can be same as those shown in FIG. 1. Inside the supporting frame 1, a rotational frame 15 is supported by the supporting frame through the bearings 4, 4 in a freely rotatable manner and the belt pulley 11 is fitted onto the outer periphery at one end of the rotational frame 15. A hollow shaft 16 is placed inside the rotational frame 15 so as to be supported by the rotational frame 15 through the flaw detection signal repeater 7 and allows the material 5 to be probed to pass through the bore of the hollow shaft. A searching unit holder 17 is disposed in the hollow shaft 16 through the flaw detection signal repeater 7; extends in the longitudinal direction of the hollow shaft 16 and rotates in association with the hollow shaft 16. A sensor 18 comprising ultra-sonic searching units (hereinafter referred to as ultra-sonic searching units) is incorporated in the searching unit holder 17.

A reference numeral 19 designates a signal transmission device to transmit flaw detection signals from the ultra-sonic searching units 18 to the outside. The signal transmission device is placed between the hollow shaft 16 and the rotational frame 15 and comprises a stator section 19b supported by the supporting frame 1 through a supporting member 20 and a rotor section 19a which is supported by, for example, the hollow shaft 16, opposing the stator section 19b and is electrically associated with the stator section 19b.

In the following, the operations of the automatic flaw detection apparatus according to the present invention will be described. First of all, the drive motor 12 is actuated to rotate the rotational frame 5 through the belt 13 and the belt pulley 11. The rotation of the rotational frame causes the rotation of the hollow shaft 16. In association with rotation of this hollow shaft 16, there rotate both searching unit holder 17 which is disposed inside the hollow shaft 16 extending in the longitudinal direction through the flaw detection signal repeater 7 and ultra-sonic searching units 18 incorporated in the searching unit holder 17. Subsequently, the material 5 to be probed is conveyed from the inspection line and passed through the center of the searching unit holder 17 upon alignment of the material 5 to be probed by means of the pinch rollers 14. When the material 5 to be probed is passing through the center of the searching unit holder 17, water for the flaw detection is supplied from the water supply device 10 into a space gap between the ultra-sonic searching units 18 and the material 5 to be probed, and filled in it. Thus, by passage of the material 5 to be probed through the center of the searching unit holder 17 in rotation, the material 5 to be probed is searched in a spiral form by the ultra-sonic searching units 18 incorporated in the searching unit holder 17. The flaw detection signals from the ultra-sonic searching units 18 are transmitted from the rotor section 19a of the signal transmission device 19 to its stator section 19b by way of the flaw detection signal repeater 7, after which it is led outside.

Figure 3:
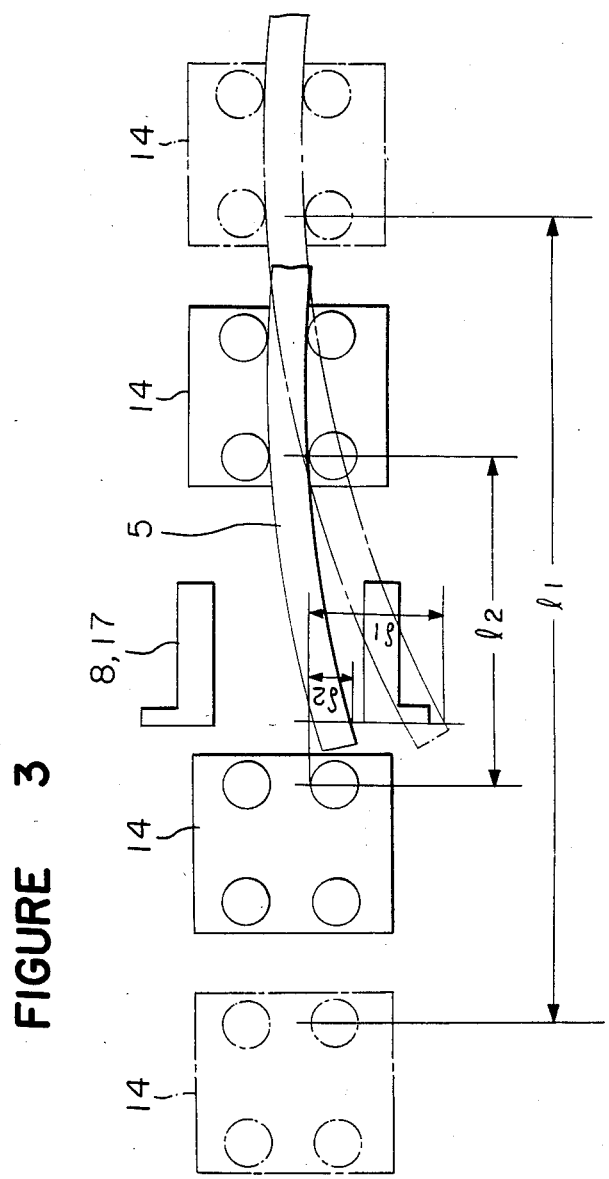
FIG. 3 is a schematic side view showing modes of curving of the material to be probed.

Incidentally, since the rotational frame 15 is disposed inside the supporting frame 1 through the bearings 4; the hollow shaft 16 is arranged inside the rotational shaft 15; the searching unit holder 17, in which the ultra-sonic searching units 18 are incorporated, is disposed inside the hollow shaft 16 extending along the lengthwise direction thereof, and the signal transmission device 19 is placed between the hollow shaft 16 and the rotational frame 15, the total length of the device can be made short. Along with this shortening of the length of the flaw detection device, the spacing for arranging the pinch rollers 14, 14 is also shortened from $l_1$ to $l_2$ as shown in FIG. 3, whereby the deflecting quantity of the material 5 to be probed due to its curving can also be made small from its value $\delta_1$ to $\delta_2$, hence the material 5 to be probed can be searched without its getting in contact with the searching unit holder 17. Further, it is feasible with this device to perform search of the material 5 to be probed with its permissible amount of deflection or curving having been made large.

Incidentally, the signal transmission device 19 in the above-described embodiment may be constructed in such a manner that the rotor section 19a is made of a slip-ring and the stator section 19b of a brush. Or, it may be of a transformer constructed in such a manner that the rotor section 19a is made of a rotary winding and the stator section 19b of a fixed winding. In either case, there can be obtained the same effect as that of the above-described embodiment.

In the above-described embodiment according to the present invention, explanations have been made as to the automatic flaw detection device by use of the ultra-sonic probing technique. It should, however, be noted that the present invention is not limited to this embodiment alone, but it is applicable to other probing techniques. For example, the present invention is also applicable to an automatic flaw detection device by use of the magnetic probing technique, an automatic flaw detection device by use of the electrical probing technique, an automatic flaw detection device by use of the optical probing technique, and so forth.

As has been described so far, according to the present invention, the automatic flaw detection device of a shortened total length can be realized by supporting the rotational frame inside the supporting frame through the bearings in a freely rotatable manner, by placing the hollow shaft inside the rotational frame so as to be held by the same, by disposing inside the hollow shaft the holder incorporating therein a sensor so as to be rotated in association with the hollow shaft and extending along the longitudinal direction thereof and by disposing the signal transmission device comprising the stator section supported by the supporting frame and the rotor section supported by the hollow shaft or the rotational frame, between the hollow shaft and the rotational frame.

Although the present invention has been described in the foregoing with particular reference to the preferred embodiment thereof, it should be noted that any changes and modifications may be made by those persons skilled in the art without departing from the spirit and scope of the invention as recited in the appended claims.

What is claimed is:

1. An automatic flaw detection apparatus for detecting flaws in a piece of material which is elongated in a first direction, comprising:

two sets of pinch rollers for supporting said material, which are aligned in said first direction to move said material in said first direction;

a fixed supporting frame being placed between said sets of pinch rollers and around said material, having a length in said first direction which is less than the distance between said sets of rollers;

a rotating frame inside said supporting frame and around said material, having a length in said first direction of about the same length as said supporting frame;

bearings mounted between said supporting frame and said rotating frame to allow said rotating frame to rotate freely;

motor means mounted on said supporting frame;

power transmission means connecting said motor means and said rotating frame for driving said rotating frame;

a hollow shaft mounted inside said rotating frame and around said material, having a length in said first direction of about the same length as said supporting frame and said rotating frame;

a flaw detection signal repeater extending from said hollow shaft to said rotating frame so that said hollow shaft is supported by said rotating frame therethrough and is rotated with said rotating frame;

a searching unit holder inside said hollow shaft and around said material, having a length in said first direction of about the same length as said supporting frame, said rotating frame and said hollow shaft, said searching unit holder being supported by said hollow shaft and rotated therewith;

ultrasonic searching units contained in said searching unit holder for detecting flaws in said material;

signal transmission device having a first part fixedly connected to said hollow shaft on the surface of said hollow shaft facing said rotating frame, and a second part mounted on a supporting member connected to said supporting frame, said supporting member extending between said rotating frame and said hollow shaft so as to be adjacent to said first part, so that signals may be transmitted therethrough;

a water supply mounted on said supporting frame in communication with a water channel connected to said hollow shaft and said searching unit holder, so as to provide water to the space to the space between said material and said searching unit holder;

said supporting frame, said rotating frame, said hollow shaft and said searching unit holder being concentrically arranged about said material so as to provide a short distance between said sets of pinch rollers so that curving of the material between the pinch rolers is minimized.

2. An automatic flaw detection apparatus according to claim 1, wherein said signal transmission device is a transformer formed of a rotary winding as said rotor section and a fixed winding as said stator section.

3. An automatic flaw detection apparatus according to claim 1, wherein said signal transmission device is constructed by a slip-ring as said rotor section and a brush as said stator section.

4. An automatic flaw detection apparatus according to claim 1, wherein said sensor comprises ultra-sonic searching units and water for detection is supplied so as to fill a space gap between said ultra-sonic searching units and said holder.

* * * * *